(12) United States Patent
Omtveit et al.

(10) Patent No.: US 7,826,880 B2
(45) Date of Patent: Nov. 2, 2010

(54) ELECTROCHEMICAL SENSOR FOR IN-VIVO OR EX-VIVIO MEASUREMENTS OF THE CARBON DIOXIDE PARTIAL PRESSURE OF LIVING TISSUE

(75) Inventors: Tore Omtveit, Eiksmarka (NO); Peyman Mirtaheri, Oslo (NO)

(73) Assignee: Alertis Medical AS (NO)

( * ) Notice: Subject to any disclaimer, the term of this patent is extended or adjusted under 35 U.S.C. 154(b) by 172 days.

(21) Appl. No.: 11/632,575

(22) PCT Filed: Jul. 18, 2005

(86) PCT No.: PCT/GB2005/002820

§ 371 (c)(1),
(2), (4) Date: May 22, 2007

(87) PCT Pub. No.: WO2006/008505

PCT Pub. Date: Jan. 26, 2006

(65) Prior Publication Data

US 2008/0011615 A1    Jan. 17, 2008

(30) Foreign Application Priority Data

Jul. 16, 2004    (GB) .................... 0416004.0

(51) Int. Cl.
*A61B 5/05* (2006.01)

(52) U.S. Cl. .................. 600/353; 600/345; 600/348; 600/364

(58) Field of Classification Search .......... 600/348, 600/353

See application file for complete search history.

(56) References Cited

U.S. PATENT DOCUMENTS

| 4,197,853 | A |   | 4/1980 | Parker |
|-----------|---|---|--------|--------|
| 4,324,256 | A |   | 4/1982 | Vesterager |
| 4,452,672 | A |   | 6/1984 | Parker et al. |
| 4,846,937 | A | * | 7/1989 | Driscoll et al. ........... 205/782.5 |
| 5,244,561 | A |   | 9/1993 | Calzi et al. |
| 5,526,809 | A |   | 6/1996 | Fiddian-Green |
| 6,541,268 | B1 |  | 4/2003 | Tonnessen et al. |

FOREIGN PATENT DOCUMENTS

| GB | 1 314 877 GBX |   | 4/1973 |
|----|---------------|---|--------|
| GB | 1 368 870     |   | 10/1974 |
| JP | 56070756      |   | 6/1981 |
| JP | 58058457      |   | 4/1983 |
| JP | 62259053      |   | 11/1987 |
| JP | 07231885      |   | 9/1995 |
| WO | WO 91/06241   |   | 5/1991 |
| WO | WO 00/04386   | * | 1/2000 |
| WO | WO 2005/039405 |  | 5/2005 |

* cited by examiner

*Primary Examiner*—Patricia C Mallari
(74) *Attorney, Agent, or Firm*—Cantor Colburn LLP

(57) ABSTRACT

A physiological sensing device for the measurement of pCO2 includes a closed chamber bounded, at least partially, by a carbon dioxide permeate e membrane (12). There are two electrodes (10) within the chamber. The chamber contains a substantially electrolyte-free liquid in contact with electrodes (10) and the membrane (12). The liquid contains a non-ionic excipient in order to prevent egress of water due to an osmotic gradient across the membrane (12) in use.

4 Claims, 3 Drawing Sheets

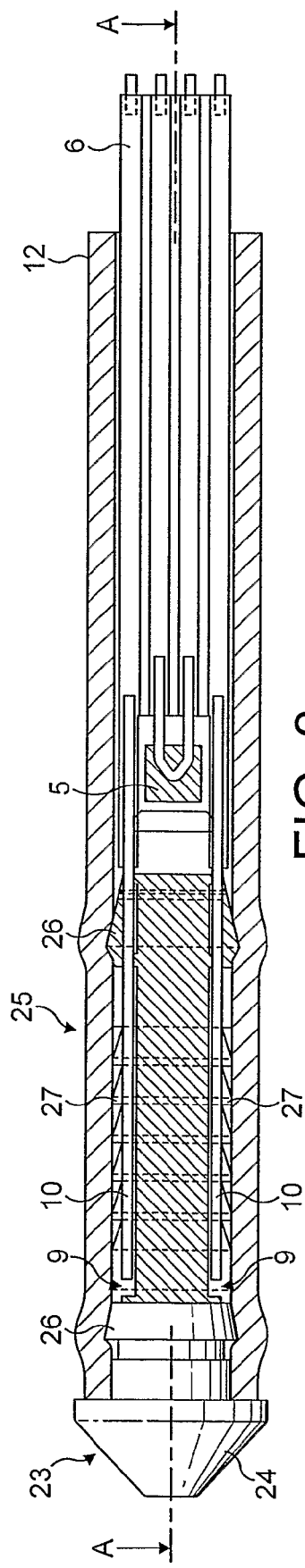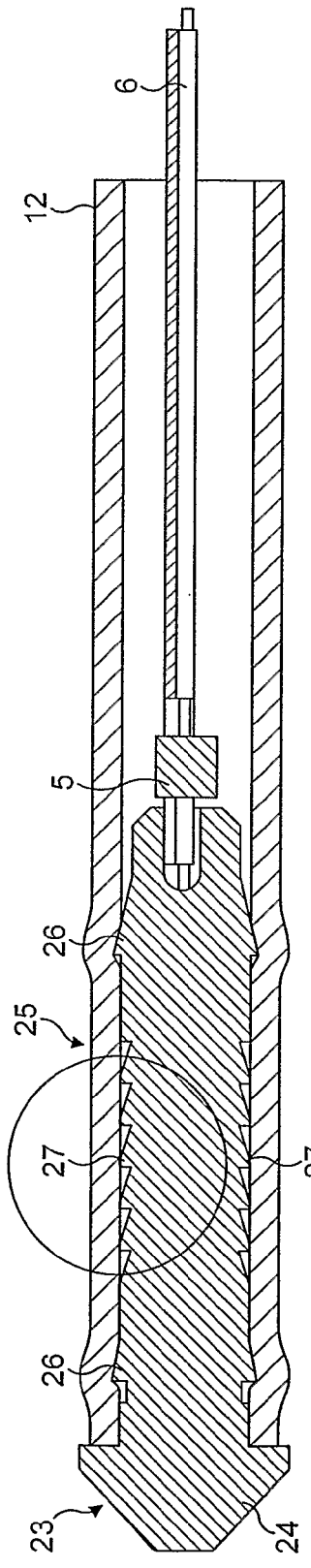
FIG. 3
FIG. 4

ELECTROCHEMICAL SENSOR FOR IN-VIVO OR EX-VIVIO MEASUREMENTS OF THE CARBON DIOXIDE PARTIAL PRESSURE OF LIVING TISSUE

TECHNICAL FIELD OF THE INVENTION

The invention relates to a physiological sensor, in particular for the partial pressure of carbon dioxide ($pCO_2$), for example in vivo or ex vivo, e.g. in or on the surfaces of body tissues or organs.

DESCRIPTION OF THE RELATED ART

Ischemia is a medical term for a shortage of blood supply to an organ. If severe, it can lead to death of the affected tissue (infarction). A sensor can be provided to measure tissue $pCO_2$, which is a parameter that increases significantly during the early and reversible stages of ischemia. Such a sensor preferably provides the ability to identify the onset of ischemia events through real-time data.

Ischemia is the most prevalent cause of death in the western world. Thus, for example, myocardial infarction, cerebral infarction and other conditions characterised by hypoperfusion to one or more organs are major factors in mortality.

Reperfusion, reversal of ischemia, is frequently possible if an ischemia is detected in time. Thus, early detection of ischemia followed by appropriate chemical treatment (e.g. with an agent such as streptokinase, urokinase or t-PA which serves to lyse thrombi or emboli) or surgical intervention can save the affected organ as well as the patient's life.

While the heart may be monitored continuously for ischemias using an electrocardiograph (ECG), other organs may become severely ischemic and incur irreversible damage before any symptom is detected. Indeed many organs are "silent" when it comes to ischemia. The phenomenon of silent myocardial infarction is now well recognised. Furthermore, liver and kidney may be severely ischemic without alerting symptoms before the organ damage is irreversible.

It is known that there is a distinct correlation between $pCO_2$ in or on the surface of an organ and the presence of an ischemia in that organ. During tissue metabolic acidosis, e.g. during the anaerobic metabolism that occurs in an ischemia in any organ or tissue, large quantities of carbon dioxide are formed. $CO_2$ is in practical terms freely cell-membrane permeable and since in the ischemia blood flow to transport away the $CO_2$ is absent or restricted, $CO_2$ build up in the ischemic tissue will occur and $pCO_2$ in or on the ischemic tissue will increase. Generally, in the healthy body, the maximum $pCO_2$ in blood (venous blood) is 7-10 kPa and the maximum $pCO_2$ in healthy (aerobic) tissue is some 1-6 kPa higher, although the maxima may vary from organ to organ, e.g. 8-12 kPa for kidney, 7-11 kPa for liver, 8-12 kPa for intestinal serosa, and 12-19 kPa for intestinal mucosa. Where oxygen supply falls below the critical oxygen delivery level, $pCO_2$ values measured in the tissue may rise by 3 to 10 times and the elevated $pCO_2$ levels give a clear indication of anaerobic metabolism and hence, if appropriate, of ischemia.

A simple sensor particularly suitable for $pCO_2$ measurement, especially as part of a technique for monitoring for ischemias, is described in WO 00/04386.

The sensor comprises a closed chamber bounded, at least partially, by a substantially water-tight, carbon dioxide-permeable membrane. The chamber contains at least two electrodes and a film of substantially electrolyte-free liquid, such as de-ionised water. The liquid contacts the membrane and both electrodes, so that carbon dioxide crossing the membrane increases the concentration of bicarbonate ions in, and hence the conductivity of, the liquid.

The inventors have identified that in some circumstances even a substantially water-tight membrane may allow fluid transport across the membrane if there is a sufficiently large osmotic gradient across the membrane. For example, if the sensor is used in vivo, a sufficiently large osmotic pressure may be caused across the membrane by the difference in osmolality between the body and the liquid in the chamber to cause water to cross the membrane. This is undesirable as the concentration of bicarbonate ions in the chamber will be affected.

The present invention seeks to address this newly-identified problem.

BRIEF SUMMARY OF THE INVENTION

Viewed from a first aspect, the invention provides a physiological sensing device for the measurement of $pCO_2$, the device comprising:

a closed chamber bounded, at least partially, by a carbon dioxide permeable membrane; and at least two electrodes within the chamber, wherein the chamber contains a substantially electrolyte-free liquid in contact with the electrodes and the membrane and wherein the liquid contains a non-ionic excipient.

Thus, according to the invention, the liquid in the chamber contains a non-ionic excipient. In this way, the osmolarity of the liquid in the chamber can be increased to prevent egress of the liquid across the membrane, without affecting the electrical characteristics of the liquid.

The excipient should have at least isotonic concentration, i.e. should be isosmotic with an aqueous solution of 0.9% w/v NaCl. Thus, the osmolality of the excipient in the chamber may be greater than that of 0.9% w/v aqueous NaCl, preferably greater than that of 1.8% w/v aqueous NaCl (twice isotonic concentration). Osmolalities greater than that of 4.5% w/v aqueous NaCl (five times isotonic concentration), or even greater than that of 9% w/v aqueous NaCl (ten times isotonic concentration) may be used.

Any suitable excipient may be used that is insert to the bicarbonate reaction in the chamber. The excipient should also be soluble in the liquid, for example water. The excipient is also desirably an accepted pharmaceutical excipient for intravenous use and with low viscosity for simple filling of the chamber. The excipient should preferably be sterilizable and storage stable. Desirably, the excipient should inhibit microbiological growth.

A suitable excipient is polyethylene glycol (PEG) and the presently preferred excipient is propylene glycol.

By substantially electrolyte-free, it is meant that the liquid has an ionic osmolality no greater than that at 37° C. of an aqueous 5 mM sodium chloride solution, preferably no more than that of a 500 μM sodium chloride solution, more especially no more than that of a $10^{-5}$ to $10^{-6}$ M HCl solution.

Preferably, the liquid in contact with the electrodes is aqueous and especially preferably it is water, substantially electrolyte-free as defined above. Other solvents that react with $CO_2$ to increase or decrease their conductance, e.g. by the production or neutralization of ions, may likewise be used. In practice, however, deionized or distilled water with or without the addition of a strong acid (e.g. HCl) to a concentration of 0.1 to 100 μM, preferably 0.5 to 50 μM, more especially about 1 μM, has been found to function particularly well. The function of this small addition of acid is generally to maintain the pH of the liquid at 6 or below to avoid significant contributions to conductance by hydroxyl ions and to maintain the linearity of the measurements of $pCO_2$.

The primary components of the $pCO_2$ sensor are an electrode chamber, a $CO_2$-permeable membrane forming at least part of the wall of the electrode chamber, first and second electrodes having surfaces within said chamber (or providing internal surfaces to said chamber), and a liquid (generally substantially electrolyte-free water) in the electrode chamber in contact with the membrane and the first and second electrodes. The sensor includes or is connectable to an AC power supply, a conductance (or resistance) determining device, a signal generator (which may be part of the determining means) and optionally a signal transmitter.

The mechanism by which $pCO_2$ is determined using the sensor device of the invention is straightforward. In a pure protic solvent, e.g. water, the electrical resistance is high because of the paucity of ionic species. Addition of $CO_2$ results in formation (with water) of $H^+$ and $HCO_3^-$ ions and thus a reduction in the electrical resistance. Since the only factor responsible for reduction in resistance in the sensor is $CO_2$ passing through the membrane, the change in resistance enables $pCO_2$ to be measured.

From the equilibrium constant for the $H_2O + CO_2$ to $H^+ + HCO_3^-$ equilibrium, $CO_2$ concentration is equal to $\alpha pCO_2$ (where a at 25° C. is 0.310). The electrical conductivity for protons is $G_{H+}=349.8$ S.cm$^2$/mol, that for hydroxyls is $G_{OH-}=198.3$ S.cm$^2$/mol and that for bicarbonate is $G_{HCO3-}=44.5$ S.cm$^2$/mol. The concentrations of $H^+$ and $OH^-$ vary inversely, and the concentrations of $H^+$ and $HCO_3^-$ are directly proportional to $pCO_2$. The total conductance of the solution is thus effectively proportional to $pCO_2$ since the contribution of $OH^-$ is minimal. The conductivity of the solution $G_{solution}$ is thus given by $$G_{solution} = \theta_{H+}[H^+]G_{H+} + \theta_{OH-}[OH^-]G_{OH-} + \theta_{HCO3-}[HCO_3^-]G_{HCO3-}$$

where $\theta_{H+}$, $\theta_{OH-}$ and $\theta_{HCO-}$ are the activity coefficients for the three ionic species.

Table 1 below shows, by way of example, measured $pCO_2$ and pH values and corresponding calculated values for $H^+$, $OH^-$ and $HCO_3^-$ concentrations showing the increase of $H^+$ and $HCO_3^-$ with increasing $pCO_2$.

| Sample number | $pCO_2$ (kPa) | pH | [H$^+$] (mmol/l) | [OH] (mmol/l) | [HCO$_3$] (mmol/l) |
|---|---|---|---|---|---|
| 1 | 6.38 | 5.141 | 7.23E−06 | 1.38E−09 | 7.23E−06 |
| 2 | 9.64 | 5.060 | 8.71E−06 | 1.15E−09 | 8.71E−06 |
| 3 | 15.37 | 4.891 | 1.29E−05 | 7.78E−10 | 1.29E−05 |
| 4 | 25.88 | 4.760 | 1.74E−05 | 5.75E−10 | 1.74E−05 |
| 5 | 31.48 | 4.664 | 2.17E−05 | 4.61E−10 | 2.17E−05 |

($pCO_2$ and pH measured with a standard blood gas analyser, ABL® System 625 at 37° C.)

The electrical conductivity is measured in the solvent film in the sensor of the invention. This can be done by applying a constant voltage (or current) to the electrodes and measuring the current (or voltage) changes which correspond to changes in conductivity as $CO_2$ enters the solvent through the membrane. Preferably however an alternating sine wave function voltage with a constant peak value is applied and the voltage drop across the electrodes is measured. The solution conductivity is then equal to the current passed through the electrode divided by the voltage drop across the electrodes.

The $pCO_2$ sensor may function by applying an alternating electrical potential to the electrodes whereby to cause an alternating current in the liquid. The liquid should be reactive with carbon dioxide to alter its conductance. The electrical potential may have a frequency of 20 to 10,000 Hz, preferably 100 to 4,000 Hz.

The $pCO_2$ sensors of the invention are provided with or are connectable to an electrical power source arranged to apply an alternating electrical potential across the electrodes with a frequency of 100 to 10,000 Hz. The frequency is preferably greater than 1 kHz. The frequency is preferably less than 5 kHz, more preferably less than 2 kHz. At frequencies below 100 Hz, the sensitivity of $pCO_2$ determination is lower due to electropolarization and moreover the instrument response time becomes overly slow, while at frequencies above 10 kHz sensitivity is again less due to the low impedance of the capacitances in the sensor.

The power source may be an AC power source or alternatively a DC source in conjunction with an oscillator, i.e. a combination which together constitutes an AC power source.

The power supply is preferably such that the maximum current density through the liquid at the electrodes is no more than 50 A/m$^2$, preferably no more than 30 A/m$^2$, more preferably no more than 20 A/m$^2$, in particular no more than 10 A/m$^2$, and most preferably about 1 A/m$^2$ or below. Higher current density values of 20 A/m$^2$ or greater should only be used at the higher frequencies, e.g. 1-10 kHz. The smallest maximum current density is determined by detection limits, but values down to 10$^{-8}$ A/m$^2$ are usable. The smallest maximum current density however will generally be at least 0.1 μA/m$^2$.

By operating at such current densities and voltage frequencies, and by appropriate construction, the sensor can determine the conductance/resistance of the liquid into which the $CO_2$ migrates without any significant loss of accuracy arising as a result of the electropolarization of the electrodes.

For particularly high accuracy, the potential or current across the electrodes (and hence the resistance or conductance of the liquid between the electrodes) is determined using a lock-in amplifier set to the same frequency as that of the voltage generator or electrical power source.

Furthermore it is preferred to incorporate in the detection a high pass filter to screen out current with a frequency less than 100 Hz, preferably less than 150 Hz. The filter is preferably a passive filter, for example a capacitor and a resistor.

The power source and the detector circuitry may, if desired, be included in the sensor of the invention. In this case, if it is desired that the sensor be wireless, it will preferably also be provided with means enabling the signal to be detected remotely, e.g. a transmitter, for example a RF transmitter. In this way the sensor may be implanted, for example in an at-risk patient.

A further electrode may be provided that is electrically connected to the patient, for example to the patient's skin. The signal from this further electrode may be processed with the signal from the sensor in order to compensate for electromagnetic noise from the patient.

Electropolarization effects are considerably reduced by increasing the surface area of the electrodes in contact with the liquid, e.g. by siting the electrodes in wells disposed away from the plane of the membrane or by using non-planar electrode surfaces, e.g. rough or textured surfaces. In general therefore it is desirable to have as large a ratio of surface area of electrode to liquid contact as possible, and as shallow as possible a liquid depth over as much as possible of its area of contact with the membrane. In this way the response time is reduced, electropolarization is reduced, lower frequencies may be used and stray capacitance effects are considerably reduced.

Increased electrical resistance relative to the resistance at the electrodes may be achieved by restricting the cross sectional area of the electrical path through the liquid between the electrodes at a zone in which the liquid is in contact with the membrane, e.g. by decreasing the depth of the liquid for a part of the path between the electrodes, and/or by ensuring a relatively large area of contact between each electrode and the liquid.

The resistance of the liquid at the membrane and between the electrodes may be increased by the use of structural elements to define liquid channels across the membrane between the electrodes, e.g. by disposing the membrane across or adjacent an insulating chamber wall portion in which such channels are formed, for example by etching. Likewise a porous spacer may be disposed between the membrane and the chamber wall to define the depth of the liquid.

Indeed, such spacers are important to use where, under the pressure conditions experienced in use, the membrane is sufficiently flexible and the liquid depth behind the membrane sufficiently small, for the measured conductance to vary with pressure.

In a preferred arrangement, the sensor comprises:

a sensor body having a longitudinal axis;

at least two electrodes spaced in a direction transverse to the longitudinal axis of the sensor body;

a plurality of support members extending outwardly from the axis of the sensor body and defining between adjacent support members at least one liquid channel that provides a fluid pathway between the electrodes; and a gas-permeable membrane supported by the support members and providing an outer wall of the liquid channel(s).

This arrangement provides a compact configuration of the sensor with a longitudinal geometry that is suited to insertion in an organ. Furthermore, the support members are able to provide physical support to the membrane, as well as defining liquid channels of small cross-sectional area that allow accurate measurement.

In order to reduce the electropolarisation effect mentioned above, the electrodes may be located in a recess in the sensor body that has a greater cross-sectional area than the liquid channels. In this way, the current density around the electrodes is reduced by the greater volume for liquid.

The electrodes of the sensor may extend longitudinally, for example parallel to the longitudinal axis of the sensor body.

Similarly, the liquid channel(s) may be transverse, for example perpendicular, to the longitudinal axis of the sensor body. In a preferred arrangement, the sensor comprises a plurality of liquid channels. For example, the sensor may comprise at least three liquid channels.

The support members may be transverse to the longitudinal axis of the sensor body. For example, the support members may be perpendicular to the longitudinal axis of the sensor body in the circumferential direction. In a preferred arrangement, the support members are in the form of rings formed about the longitudinal axis of the sensor body. The cross-section of the support members may be any suitable shape. It has been found in particular that support members with a substantially triangular, in particular sawtooth, cross-section are particularly easily formed by injection moulding. Alternatively, a substantially rectangular cross-section may be used. The support members may be formed integrally with the sensor body, for example by injection moulding. The sensor preferably comprises at least four support members.

The sensor body and/or the sensor may be generally cylindrical. The membrane may be arranged to surround the sensor body.

The described geometry may be applied to any suitable sensor. In the preferred arrangement, the sensor is a $pCO_2$ sensor.

Where the sensor is constructed with the liquid film in place, the electrodes are preferably of, or plated with, an inert material such that the resistivity of the liquid will not change significantly with storage. Suitable materials include platinum (especially black platinum), gold, silver, aluminium and carbon. Gold is particularly preferred. In general inert electrodes which do not generate solvated ions are preferred.

The membrane may be any material which is permeable to $CO_2$, and substantially impermeable to the solvent of the liquid, any electrolyte and water. Polytetrafluoroethylene, e.g. Teflon®, silicone rubber, polysiloxane, polyolefins or other insulating polymer films may be used, e.g. at thicknesses of 0.5 to 250 µm. The thicker the membrane, in general the slower the response time of the sensor will be. However the thinner the membrane the greater the risk of non-uniformities or of perforation or other damage. Conveniently however the thickness of the membrane will be 1 to 100 µm, preferably 50 to 100 µm.

The walls of the chamber of the sensor of the invention may be of any suitable material, e.g. plastics. Preferably the material should be capable of withstanding conditions normally used in sterilisation, e.g. radiation sterilization (for example using gamma radiation) or thermal sterilization (for example using temperatures of about 121° C. as used in autoclave sterilisation). In the case of thermal sterilization, the liquid will generally be sterile filled into the sensor after sterilization. The walls of the chamber and the membrane may be of the same material, e.g. Teflon®, machined to have self-supporting walls and a thinner gas-permeable membrane.

The sensors of the invention are generally relatively inexpensive and so, unlike prior art sensors, may be single-use devices. Moreover the electrode chamber can be made extremely small without difficulty (unlike the prior art glass electrode containing sensors for which miniaturization poses insuperable impedance problems).

This arrangement provides a sensor, in particular, a $pCO_2$ sensor, which can be inserted easily into the tissue of an animal, including a human, which can be retained in the tissue during monitoring and which can be removed easily when monitoring is complete.

The device is sufficiently small that it will not cause undue disturbance to the tissue to be monitored. Consequently, the device may have a maximum diameter of 2 mm, preferably 1 mm.

The sensors according to the invention are readily produced having a size and configuration particularly suited to measuring $pCO_2$ on the surface of or in an organ, duct or tissue, e.g. brain, heart, liver, kidney, gut or muscle. This is of particular interest as it allows the functioning of the organ, duct or tissue to be monitored, e.g. during and after transplant, in intensive care, following injury, etc. and so allows early detection of ischemias.

The partial pressure determined by the sensor may be a quantified value or it may simply be an indication that $pCO_2$ is above or below one or more threshold values indicative of ischemia or non-ischemia, values which may be varied according to the location of the $pCO_2$ measurement site.

The sensor may be used for a single measurement of $pCO_2$ or, more preferably, may be used for continuous or repeated monitoring, especially of an at-risk patient, for example a patient in intensive care, undergoing or recovering from an organ or tissue transplant operation, assessed as having unstable angina, recovering from a coronary artery bypass operation, suffering trauma (e.g. of skeletal muscle), or suffering from hypovolemia (e.g. shock).

The device may comprise a plurality of sensors for respective physiological parameters. For example, the device may comprise an array of sensors. Such sensors may measure one or more of the partial pressure of carbon dioxide, the partial pressure of oxygen, temperature, pH or glucose concentration, for example. In the presently preferred embodiment, the device comprises a temperature sensor and a $pCO_2$ sensor.

BRIEF DESCRIPTION OF THE DRAWINGS

An embodiment of the invention will now be described, by way of example only, with reference to the accompanying drawings, in which:

FIG. 3 is a partially cutaway view of a sensor according to the invention;

FIG. 4 is a cross-sectional view along line A-A of FIG. 3;

DETAILED DESCRIPTION OF THE INVENTION

Figure 1:
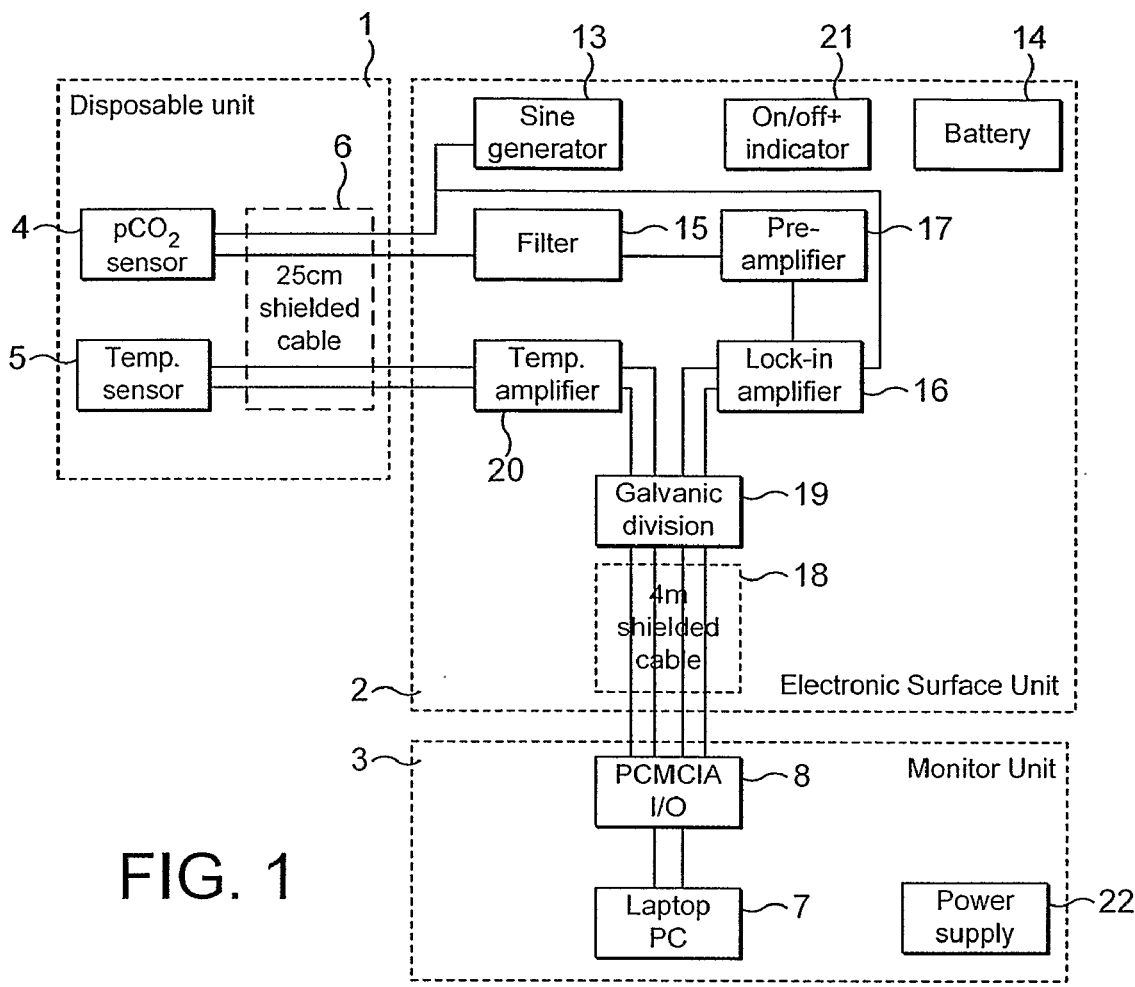
FIG. 1 is a schematic diagram of a complete sensing system incorporating the sensor of the invention.

In accordance with the invention, a $pCO_2$ sensing system comprises a disposable sensor unit 1, an electronic surface unit 2, and a monitor unit 3, as shown in FIG. 1.

The disposable sensor unit 1 is delivered packaged and sterilised. It consists of a membrane-protected conductometric sensor 4 with a diameter of less than 1 millimetre, and a temperature probe 5 integrated in the sensor unit. Wires 6 connect the sensor 4 and probe 5 electrically by means of a connector to the electronic surface unit 2. Alternatively, a wireless connection may be provided between the sensor unit 1 and the surface unit 2.

The electronic surface unit 2 sends and receives signals to and from the sensor unit 1. It is placed on the patient's skin, performs signal processing and transmits the conditioned signal to the monitor unit 5.

The monitor unit 3 is based on a portable personal computer 7 with PCMCIA input/output card 8 and Labview software (available from National Instruments Corporation of Austin, Tex.).

Figure 2:
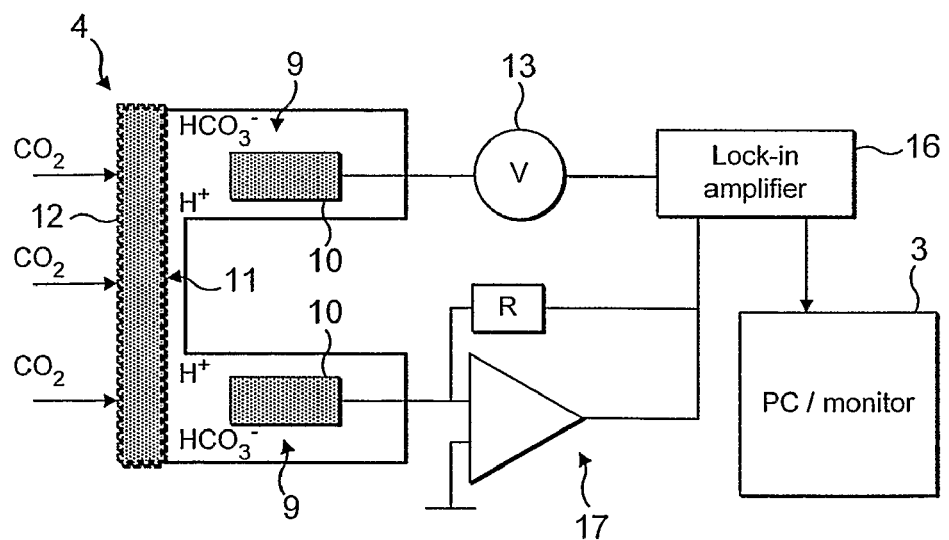
FIG. 2 is a schematic diagram illustrating the measurement principle for the sensor in the system of FIG. 1.

The $pCO_2$ sensor 4 is used for measurements of the level (partial pressure) of $CO_2$ ($pCO_2$) in a fluid, according to the measurement principle illustrated in FIG. 2. The measurement chamber consists of two small cavities 9 with one electrode 10 positioned in each. The two cavities 9 are connected by one or more passageways 11 enclosed by a semi-permeable membrane 12, i.e. a membrane that only allows transport of $CO_2$ in and out of the volume of the sensor 4. The whole volume is filled with de-ionised water and 5% propylene glycol. The conductivity in the water depends upon the $pCO_2$, and by measuring the conductivity between the electrodes 10 in the volume, information about $pCO_2$ may be extracted.

Figure 4A:
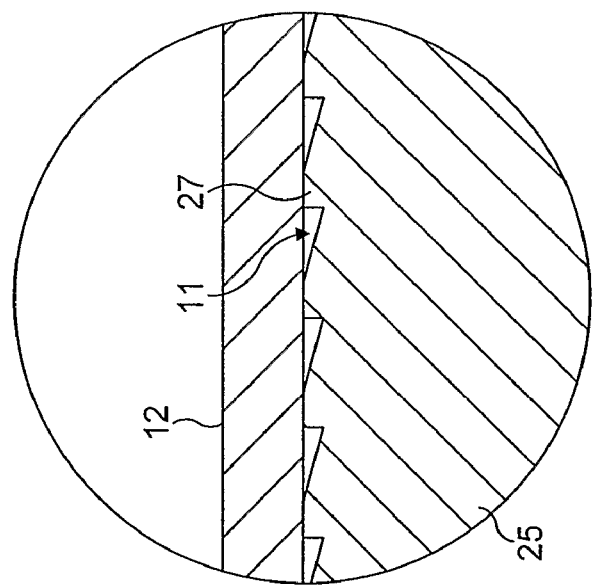
FIG. 4a is a magnified view of the detail indicated by the circle in FIG. 4.
Figure 5:
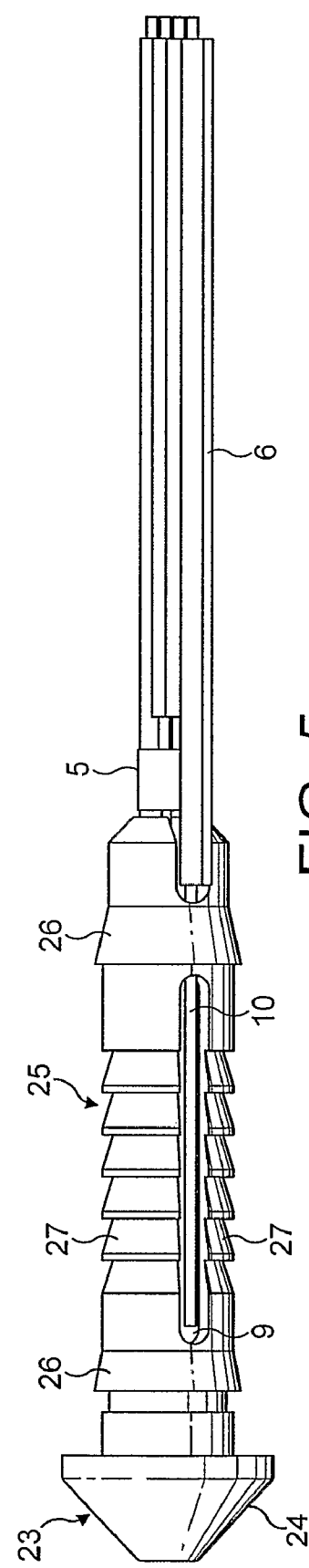
FIG. 5 is a view of the sensor of FIG. 3 with the membrane removed.

As shown in FIGS. 3 to 5, the sensor unit 1 comprises an injection moulded plastics support 23, which is substantially cylindrical and surrounded by the semi-permeable membrane 12. The support 23 has a conical tip 24 at its distal end and a body portion 25 which extends proximally from the tip 24. On the body portion 25 are mounted, by gluing, two gold electrodes 10. The electrodes 10 extend longitudinally along opposed sides of the body portion 25 and are received in respective recesses in the body portion 25.

Between the tip 24 and the body portion 25, a frustoconical projection 26 is provided for securing the membrane 12 by frictional fit. A corresponding projection 26 is provided at the proximal end of the body portion 25. The membrane 12 may be glued to the support 23, but it is important that the glue used to secure the membrane 12 and electrodes 10 is selected such that it does not bleed ions into the water-filled chamber formed between the body portion 25 of the support 23 and the membrane 12. Furthermore, the sealing faces of the support 23 may be made selectively hydrophobic in order to avoid the formation of a water film into which ions may bleed.

The membrane 12 may also be secured to the support 23 by means of crimp connection and a soft gasket, if necessary. The membrane 12 may act as the gasket, particularly where the membrane 12 is formed of silicone rubber. A heat shrink sleeve may be used to form the crimp connection. Alternatively, metal crimp rings may be used in locations corresponding to those of the sealing projections 26.

The body portion 25 of the support 23 is provided with a plurality of ribs 27, which are formed with a saw tooth profile for easy moulding. The ribs 28 provide mechanical support to the membrane 12 and also define the fluid passageways 11 required for the sensor 4 to function effectively. Between each electrode 10 and the fluid passageways formed between the ribs 27 is provided a reservoir 9 formed by the recess in which the electrode 10 is located. The reservoir 9 provides a region of relatively low current density around the electrodes 10 in order to reduce electropolarisation effects.

During manufacture, the membrane 12 is fixed onto the support 23, while immersed in the de-ionised water and propylene glycol solution, so that the chamber bounded by the membrane 12, the electrodes 10, and the ribs 27 is completely filled with liquid. Thus, this chamber forms a $pCO_2$ sensor as shown schematically in FIG. 2.

It is possible for the sensor 1 to include more than one sensing chamber. For example, two parallel electrodes 10 separated by a wall member may be provided on each side of the support 23. A sensing chamber is thereby formed between one electrode 10 on one side of support 23 via the fluid passageways 11 between the ribs 27 on the top of the support 23 to one of the electrodes 10 on the other side of the support 23. A corresponding sensing chamber is provided between the remaining electrodes 10 and the fluid passageways 11 on the bottom of the support 11. An electrode 10 from each of these chambers may be electrically connected to the corresponding electrode from the other chamber, such that the electrical signal from the sensor reflects the conductivity of both chambers.

Embedded in the proximal end of the support 23 is a temperature sensor 5 in the form of a thermocouple. The temperature sensor 5 is used both for $pCO_2$ corrective calculations and for the measured tissue temperatures to be displayed on the monitor 3, which is informative for medical diagnosis. The temperature sensor 5 has a minimum measuring range of 33-42° C. and a minimum accuracy of +/−0.2° C.

A ribbon cable 6 is electrically and mechanically connected to the electrodes 10 and the temperature sensor 5. The electrodes 10 are formed as extensions of the conductors of the ribbon cable 6. Alternatively, the electrodes may be formed by plating onto the support 23. Where the cable 6 and the connection to the support 23 are sufficiently strong, the cable 6 can be used to pull the sensor unit 1 from its position of use. Alternatively, a Kevlar line may be provided, for example incorporated with the ribbon cable 6, to provide a strong external mechanical connection.

The membrane 12 may extend proximally from the support 23 with the cable 6 to form a catheter around the cable 6. Alternatively, a separate catheter 28 may be provided. In this case, the catheter 28 is bonded to the support 23 proximally of the electrodes 10 and the membrane 12.

The catheter tip with the integrated sensor 4 is placed 0.5-4 cm into organ tissue during surgical procedures to monitor ischemia during a period of up to two weeks. The sensor may be used in orthopaedic and reconstructive surgery, and in organs such as the liver, kidneys, heart muscle, brain and intestines. An insertion tool (not shown) may be used for the placement of the sensor 4, and there may be a fixation aid to keep the sensor tip in position.

The sensor unit 1 has a maximum diameter of 1 mm and the maximum distance from the catheter tip to the sensor element is 2 mm. The sensor 4 has a minimum $pCO_2$ measuring range of 2-25 kPa, with a minimum detectable $pCO_2$ difference of 0.2 kPa. The maximum response of the sensor 4 is 20 seconds. The maximum allowable measurement current is in any area of the fluid chamber is such that $j<1$ $mA/cm^2$ while the measuring input voltage is not more than 50 mV RMS.

The electrodes 10 are gold plated and their total area is approximately 0.3 $mm^2$. The measurement frequency $f_{meas}$ should be higher than 100 Hz. At lower frequencies, polarisation effects in the measurement chamber dominate the measurements. At frequencies above 10 kHz, the low impedance of the capacitances become a significant issue. The measurement resistance $R_{\_measure}$ is in the range of 500 kOhm to 7 MOhm.

The sensor 4 is electrically connected to an electronic surface unit 2 located on the patient skin by the ribbon cable 6, which has a length between 5 cm and 1 metre. The maximum diameter of the cable/catheter is 1 mm and the preferred length of the cable/catheter is 25 cm. The cable/catheter is soft and flexible so that it does not excessively disturb the neighbouring tissue and organs. The cable/catheter and its connections are also sufficiently robust to withstand the strong pulling forces which may be caused by both normal and "abnormal" use.

During sterilisation, storage and transport the sensor unit 1 is covered by deionised, sterile and endotoxin-free water to make sure that there is substantially no net loss of water from the sensor reservoir.

As shown in FIGS. 1 and 2, the electronic surface unit 2 comprises a sine generator 13 which provides a voltage of at least 5 Volts and a current supply of 50 mV, and is powered by batteries 14. A filter 15 is provided for filtering or averaging the input of the lock-in amplifier 16. A passive filter can be used which reduces the current consumption. A pre-amplifier 17 is combined with a servo mechanism to remove DC current from the signal to reduce electrolysis effects. According to the servo arrangement, the output of the pre-amplifier is fed back to its input via a low pass filter. Thus, only DC components of the output are fed back and cancel any DC current drawn through the $pCO_2$ sensor. In this way, it is ensured that there is no DC current through the $pCO_2$ sensor which would degrade the electrodes. The op-amp used in this stage consumes minimal current and has a large CMMR value. At the same time, the bias current is minimal. A lock-in amplifier 16 amplifies the AC signal from the sensor 4. This may be built with op-amps or using an IC package with at least 1% accuracy for the signal detection at frequencies lower than 1 kHz. A galvanic division 19 such as an optocoupler or a coil coupler is provided to prevent noise transfer from the monitor unit 3 and associated cabling 18. The optocoupler is normally favoured due to the noise signal ratio. A temperature signal amplification and conditioning unit 20 is provided to amplify the signal from the temperature sensor 5. The electronic unit 2 is powered by a rechargeable and changeable standard type battery 14. The battery capacity is sufficient for 14 days continuous monitoring. The surface unit 2 is also provided with an on/off indicator LED 21, and a battery status indicator (not shown). Communication between the surface unit 2 and the monitor 3 is analogue through a shielded cable 18. However, the surface unit 2 may include an analogue to digital converter such that communication between the surface unit 2 and the monitor 3 may be digital, for example by digital wire transmission or digital wireless transmission. The cable 18 is at least 4 m long and light and flexible.

As shown in FIGS. 1 and 2, an AC current is generated by sine generator 13 and fed to one of the $pCO_2$ sensor electrodes 10 and to a lock-in amplifier 16. The high-pass signal from the other $pCO_2$ electrode 10 is passed through a filter 15 to a low noise amplifier 17 and from there to the lock-in amplifier 16 where it is compared to the reference signal generated by the sine generator 13. Out of phase components, i.e. undesired components, of the signal are rejected and the remaining portion of the signal is amplified. The amplified signal is proportional to $pCO_2$ (or conductance) and is passed on for recordal or further manipulation to the monitor 3.

The surface unit 2 may also be electrically connected to a reference electrode (not shown) that is electrically connected to the patients skin. The signal from the reference electrode can be used to compensate the signals from the sensor unit 1 for the effect of electromagnetic noise generated by the patient.

A single surface unit 2 may receive signals from several sensor units 1 and provide a multiplexed output to the monitor unit 3.

The monitor unit 3 comprises a portable PC 7 including CD RW and IR port, and a PCMCIA I/O card 8 which can collect signals from at least 4 different surface units 2 simultaneously. The PCMCIA card 8 may have an integrated non-galvanic coupling. The power supply 22 for the monitor unit 3 is of a medically approved type operating on both 110V and 230V.

The software functions of the monitor unit 3 may be implemented in Labview, a software package available from National Instruments of Austin, Tex. and capable of handling up to 4 different surface units simultaneously. The software provides the facility for calibration of the sensor(s) with three calibration points and a second order calibration function. The software can be modified to support any other number of calibration points and type of calibration function. The software also has the facility to smooth the signal from the sensor 4 over defined time intervals. It is possible to have at least two alarm levels for the measurement values and two alarm levels for their gradients. The measurement value gradients are calculated for individually defined time intervals. The alarm is both visible and audible. It is possible to stop an alarm indication while keeping the other alarms active. The monitor 3 can log all measured values, parameter settings and alarms throughout a session. With a 30 second logging interval there should be a storage capacity for at least 10 two week sessions on the hard disc. The session log can be saved to a writeable CD in a format readably by Microsoft Excel.

In summary, a physiological sensing device for the measurement of $pCO_2$ includes a closed chamber bounded, at least partially, by a carbon dioxide permeable membrane. There are two electrodes within the chamber. The chamber contains a substantially electrolyte-free liquid in contact with electrodes and the membrane. The liquid contains a non-ionic excipient in order to prevent egress of water due to an osmotic gradient across the membrane in use.

The invention claimed is:

1. A physiological sensing device for the measurement of $pCO_2$, the device comprising: a closed chamber bounded, at least partially, by a carbon dioxide permeable membrane; and at least two electrodes within the chamber, wherein the chamber contains a mixture in contact with the electrodes and the membrane and inclusive of at least a first part and a second part, the first part being a substantially electrolyte-free liquid and the second part being a non-ionic excipient, wherein the non-ionic excipient is present in the electrolyte-free liquid in at least isotonic concentration, such that the osmolality of the fluid in the chamber is at least equivalent to that of 0.9% w/v sodium chloride solution.

2. A physiological sensing device as claimed in claim 1, wherein the non-ionic excipient is propylene glycol.

3. A sensor as claimed in claim 1, wherein the electrolyte-free liquid is deionised or distilled water.

4. A sensor as claimed in claim 2, wherein the electrolyte-free liquid is deionised or distilled water.

* * * * *